United States Patent
Ren et al.

(10) Patent No.: US 11,911,433 B2
(45) Date of Patent: Feb. 27, 2024

(54) PREPARATION METHOD OF NON-ESTER TEA POLYPHENOLS RICH IN EGC

(71) Applicant: JIANGSU DEHE BIOTECHNOLOGY CO., LTD., Jiangyin (CN)

(72) Inventors: Xueyin Ren, Jiangyin (CN); Jianhong Liu, Jiangyin (CN); Houjian Cao, Jiangyin (CN); Pingnan Pu, Jiangyin (CN); Dehe Liu, Jiangyin (CN)

(73) Assignee: JIANGSU DEHE BIOTECHNOLOGY CO., LTD., Jiangyin (CN)

( * ) Notice: Subject to any disclaimer, the term of this patent is extended or adjusted under 35 U.S.C. 154(b) by 0 days.

(21) Appl. No.: 18/024,758

(22) PCT Filed: Jan. 17, 2022

(86) PCT No.: PCT/CN2022/072230
§ 371 (c)(1),
(2) Date: Mar. 4, 2023

(87) PCT Pub. No.: WO2022/156615
PCT Pub. Date: Jul. 28, 2022

(65) Prior Publication Data
US 2023/0241151 A1 Aug. 3, 2023

(30) Foreign Application Priority Data

Jan. 19, 2021 (CN) .......................... 202110065862.2

(51) Int. Cl.
*A61K 36/82* (2006.01)
*A61K 31/353* (2006.01)
*A61K 36/00* (2006.01)

(52) U.S. Cl.
CPC ............ *A61K 36/82* (2013.01); *A61K 31/353* (2013.01); *A61K 2236/15* (2013.01); *A61K 2236/31* (2013.01); *A61K 2236/331* (2013.01); *A61K 2236/39* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| 6,113,965 | A | 9/2000 | Goodsall et al. | |
| 10,688,158 | B2 * | 6/2020 | Cornblatt | A61K 9/0053 |
| 10,960,057 | B2 * | 3/2021 | Cornblatt | A61K 31/716 |
| 11,224,639 | B2 * | 1/2022 | Cornblatt | A61K 9/0053 |

FOREIGN PATENT DOCUMENTS

| CN | 1626668 | A | | 6/2005 |
| CN | 102443614 | A | | 5/2012 |
| CN | 103242282 | A | | 8/2013 |
| CN | 104292200 | A | | 1/2015 |
| CN | 107232326 | A | | 10/2017 |
| CN | 109077290 | A | | 12/2018 |
| CN | 112574161 | A | * | 3/2021 |
| CN | 112574161 | A | | 3/2021 |
| JP | 2011168579 | A | | 9/2011 |

OTHER PUBLICATIONS

The Variational Regular of Endogenous Enzyme Activity During the Processing of Oolong Tea, by Yang, Weili et al., dated Dec. 31, 2004.
Optimized Extraction Conditions for EGC From Tea by Response Surface Methodology, by Wang, Xianbo et al., dated Dec. 10, 2011.
International Search Report, issued in PCT/CN2022/072230, dated Apr. 12, 2022.
Written Opinion, issued in PCT/CN2022/072230, dated Apr. 12, 2022.

* cited by examiner

*Primary Examiner* — Aaron J Kosar
*Assistant Examiner* — Randall O Winston
(74) *Attorney, Agent, or Firm* — Zhu Lehnhoff LLP

(57) ABSTRACT

A preparation method of non-ester tea polyphenols rich in EGC. Includes leaching wall-broken crushed tea leaves using endogenous hydrolytic enzymes contained in the tea leaves; refining the leached solution after filtration and concentration and purifying it by mobile leaching-water washing; concentrating and drying the purified product to obtain a non-ester tea polyphenols product rich in EGC, wherein the content of tea polyphenols is 90-99.5%, the content of EGC is greater than 80%, and the content of ester catechins EGCG+ECG is less than 10%.

8 Claims, No Drawings

PREPARATION METHOD OF NON-ESTER TEA POLYPHENOLS RICH IN EGC

TECHNICAL FIELD

The present invention belongs to the technical field of processing natural plant extracts, and particularly relates to a preparation method of non-ester tea polyphenols rich in epigallocatechin (EGC).

BACKGROUND ART

Tea polyphenols are a general term for catechins, flavonoids, phenolic acids and anthocyanidins in tea. The tea polyphenols have the main effect of anti-oxidation, with very obvious elimination of oxygen free radicals. At the same time, the tea polyphenols can inhibit and sterilize bacteria, effectively reduce the absorption of cholesterol in the large intestine, prevent and treat atherosclerosis, and enhance the body's immune ability, anti-tumor, anti-radiation, anti-aging and other effects. Because of the unique efficacy of tea polyphenols, they have been widely used in the fields of medicine, health care products and food, such as in medicine for the prevention and treatment of cardiovascular, hepatic, renal and gastrointestinal diseases, in health products as main components of products for improving human immunity, reducing blood fat, lowering blood sugar and reducing weight, and also in main components of sunscreens, shampoos and disinfectants. The addition of tea polyphenols to oil food can prevent the food from rotting and keep it fresh.

The main components of tea polyphenols are catechins. The catechins are divided into ester catechins and non-ester catechins. According to the types of catechins in the tea polyphenols, the tea polyphenols are divided into ester tea polyphenols and non-ester tea polyphenols. The two types of tea polyphenols have some differences in mouthfeel, gastric irritation and stability (water solubility). The ester tea polyphenols have stronger bitterness and astringency in taste bud irritation and stronger irritation to human gastric mucosa, and the dissolution stability of products in water solubility is worse. However, the non-ester tea polyphenols are superior to the ester catechins in terms of mouthfeel, gastric irritation and stability (water solubility). Therefore, with these advantages, the non-ester tea polyphenols have a wider application prospect in food, food additives and pharmaceutical industry. The non-ester tea polyphenols contain a variety of non-ester catechin monomers, and EGC has relatively high biological activity.

At present, the technology for preparing the non-ester tea polyphenols rich in EGC is generally as follows: the tea polyphenols are extracted from tea leaves by an extraction solvent (at least one of water, ethanol and ethyl acetate); after treatment such as filtration and concentration, some exogenous hydrolytic enzymes, etc. are added to perform hydrolysis; then the enzyme bodies are inactivated at a high temperature filtering to remove same, so as to obtain a non-ester tea polyphenol solution. The product is purified by a chromatographic separation method and dried finally to obtain a non-ester tea polyphenol product In the above-mentioned process, the exogenous hydrolytic enzyme is added, which is easy to cause contamination to the product, and poor treatment will lead to the generation of allergic source. Meanwhile, the chromatographic method is used for the preparation of the product, and the process will be relatively complicated, which is not conducive to industrial production. Also, the loss of the product in the process is relatively large, and the yield is relatively low.

SUMMARY OF THE INVENTION

It is an object of the present invention to provide a preparation method of non-ester tea polyphenols rich in EGC, without adding any exogenous hydrolytic enzyme, so as to avoid the contamination to the product by the exogenous hydrolytic enzyme. Meanwhile, the content of EGC is high, the production process is simplified, and the yield of the product is high, which is conducive to industrial production.

The technical solution adopted by the present invention to solve the above-mentioned problem is a preparation method of non-ester tea polyphenols rich in EGC including the steps of:

(1) pretreatment of tea leaves: using green tea leaves as raw materials, crushing and wall-breaking the tea leaves to obtain tea particles;

(2) endogenous enzymes enzymolysis: adding the pretreated tea particles into a dynamic extraction tank, adding deionized water, and adding a food-grade acid to adjust the pH to 2.0-6.5; and under stirring conditions, performing enzymolysis on the ester tea polyphenols in the tea leaves by the hydrolytic enzyme of the tea itself;

(3) leaching: leaching the tea leaves raw material after polyphenols with deionized water twice, filtering after the leaching, and combining the two filtrates;

(4) filtration: cooling the above-mentioned filtrate, filtering again, and collecting the filtrate;

(5) concentration: concentrating the filtrate in step (4);

(6) mobile extraction-water washing: extracting the concentrated solution in step (5) with 1-2 times volume of ethyl acetate, collecting an ethyl acetate phase, and concentrating the ethyl acetate phase to a solid content of 2-10%; then performing reverse phase extraction with 0.2-1 times volume of deionized water, collecting a water-washed phase, and performing reverse phase extraction with the same method for 1-5 times, and combining the water-washed phases; and then performing extraction with 1-2 times volume of ethyl acetate for the water-washed phase, and collecting the ethyl acetate phase;

(7) conversion and dissolving: concentrating the ethyl acetate phase finally collected in step (6) to an extractum, and then adding deionized water for dissolution to obtain a tea polyphenol aqueous solution;

(8) concentration: concentrating the aqueous tea polyphenol solution in step (7) under vacuum;

(9) drying: drying the concentrated solution in step (8) by spray drying to obtain a non-ester tea polyphenol product rich in EGC.

Preferably, 10-100 mesh screen residues of the pretreated tea particles in step (1) are not more than 40%, i.e. the 10-100 mesh screen residues of the pretreated tea particles are not more than 40%.

Preferably, the addition amount of the deionized water in step (2) is 1-5 times the volume of the pretreated tea leaves; the food-grade acid is citric acid; the stirring speed is 50-300 r/min; the enzymolysis temperature is 30-50° C.; and the enzymolysis time is 4-12 h.

Preferably, the leaching temperature in step (3) is 60-90° C., the single addition amount of deionized water is 6-10 times the mass of the tea leaves raw material, and the single leaching time is 20-60 min.

Preferably, the cooling temperature in step (4) is 30-50° C., and the filtration accuracy is 100-300 meshes.

Preferably, the concentration in step (5) specifically comprises concentrating the filtrate from step (4) to 0.5-2.5 Brix.

Preferably, the ethyl acetate extraction temperature in step (6) is 30-60° C., and the deionized water reverse phase extraction temperature is 30-60° C.

Preferably, the concentration in step (8) specifically comprises concentrating the tea polyphenol aqueous solution in step (7) to 20-50 Brix under vacuum above −0.080 MPa at 52-72° C.

The present invention uses the endogenous hydrolytic enzyme contained in the tea leaves to perform enzymolysis in advance of leaching to enzymatically hydrolyze the ester catechins in the tea leaves into non-ester catechin substances (in particular, epigallocatechin gallate (EGCG) is converted into EGC), and then perform leaching of the product. The collected leached solution is treated and then refined and purified by the mobile extraction-water washing method. The purified product is subjected to concentration and drying to obtain a non-ester tea polyphenols product rich in EGC, wherein the content of tea polyphenols is 90-99.5%, a EGC content of more than 80%, and the content of EGCG+epicatechin gallate (ECG) of the ester catechin within a controllable range (less than 10%).

The advantages of the present invention over the prior art are as follows.

(1) Without adding any exogenous hydrolytic enzyme, the ester tea polyphenols in tea leaves are hydrolyzed by using the endogenous hydrolytic enzyme contained in the tea leaves in combination with the hydrolysis system, so that the ester tea polyphenols could be converted into non-ester tea polyphenols to the maximum extent, which can increase the content of non-ester tea polyphenols and eliminate the pollution of exogenous hydrolytic enzyme to the product.

(2) The mobile extraction-water washing method is used for product purification, which not only greatly improves the content of EGC, but also simplifies the production process. It greatly reduces the loss of products and improves the yield of products, which is conducive to industrial production.

(3) The non-ester tea polyphenol product rich in EGC obtained by the preparation method of the present invention has a tea polyphenol content of 90-99.5%, a EGC content of more than 80%, and the content of EGCG+ECG of the ester catechin within a controllable range (less than 10%).

DETAILED DESCRIPTION OF THE INVENTION

Hereinafter, the present invention will be described in further detail with reference to embodiments.

Embodiment 1

A preparation method of non-ester tea polyphenols rich in EGC includes the following steps.

(1) The green tea leaves were subjected to crushing and wall-breaking treatment, and the particle size of the treated tea leaves in the range of 10-100 meshes was more than 60%, namely, 10-100 mesh screen residues of the pretreated tea particles were not more than 40%.

(2) 5.0 Kg of the pretreated tea leaves were added to a dynamic extraction tank (with stirring), 4 times the volume of deionized water was added, and the pH value was adjusted to 5.0 with citric acid, with the enzymolysis performed at a rotation speed of 100 r/min and a temperature of 40° C. for 6 hours.

(3) After that, the stirring was turned off, the deionized water was added for one leaching at 80° C., and the mass ratio of tea leaves to deionized water in the extraction tank was controlled to be 1:8, with the leaching for 30 min; at the end of the first leaching, it filtered out a filtrate, and the deionized water in the same proportion was added; and the same leaching was performed for one time, it filtered after the end of leaching, and the two filtrates were combined.

(4) The collected filtrate was cooled to 40° C., further filtered by a filter with an accuracy of 200 meshes, and the filtrate was collected.

(5) The above tea water was concentrated to 1.0 Brix by a concentrating device.

(6) The above-mentioned concentrated tea water was extracted with 1.2 times the volume of ethyl acetate at an extraction temperature of 40° C. to collect an ethyl acetate phase; the ethyl acetate phase was concentrated to a solid content of 8%, and the reverse phase extraction was performed with 0.5 times the volume of deionized water (referred to as water washing), the water washing temperature being 40° C.; the water-washed phase was separated and collected, then washed with the same method for 3 times, and all the water-washed phases were collected and combined; and it was extracted by an additional 1.5 times the volume of ethyl acetate at 40° C., and the ethyl acetate phase was collected.

(7) The collected ethyl acetate solution was concentrated to an extractum, and the same was dissolved by adding 3 L of deionized water to obtain a tea polyphenol aqueous solution.

(8) The aqueous tea polyphenol solution was concentrated under vacuum, with the degree of vacuum controlled above −0.080 MPa, the temperature being 52-72° C., and the aqueous product solution being concentrated to 35 Brix.

(9) The concentrated solution was dried by spray drying, and 305 g of powder product was collected.

The content of tea polyphenols was detected to 98.6% by the UV spectrophotometer common in the industry. By detection of HPLC, the content of EGC was 81.3%, and the content of EGCG+ECG of the ester catechin was 7.3%.

Embodiment 2

(1) The green tea leaves were subjected to crushing and wall-breaking treatment, and the particle size of the treated tea leaves in the range of 10-100 meshes was more than 60%.

(2) 5.0 Kg of the pretreated tea leaves were added to a dynamic extraction tank (with stirring), 4 times the volume of deionized water was added, and the pH value was adjusted to 6.0 with citric acid, with the enzymolysis performed at a rotation speed of 150 r/min and a temperature of 45° C. for 10 hours.

(3) After that, the stirring was turned off, the deionized water was added for one leaching at 80° C., and the mass ratio of tea leaves to deionized water in the extraction tank was controlled to be 1:10, with the leaching for 30 min; at the end of the first leaching, it filtered out a filtrate, and the deionized water in the same proportion was added; and the same leaching was performed for one time, it filtered after the end of leaching, and the two filtrates were combined.

(4) The collected filtrate was cooled to 40° C., further filtered by a filter with an accuracy of 200 meshes, and the filtrate was collected.

(5) The above tea water was concentrated to 1.0 Brix by a concentrating device.

(6) The above-mentioned concentrated tea water was extracted with 1.2 times the volume of ethyl acetate at an extraction temperature of 40° C. to collect an ethyl acetate phase; the ethyl acetate phase was concentrated to a solid content of 8%, and the reverse phase extraction was performed with 0.5 times the volume of deionized water (referred to as water washing), the water washing temperature being 40° C.; the water-washed phase was separated and collected, then washed with the same method for 3 times, and all the water-washed phases were collected and combined; and it was extracted by an additional 1.5 times the volume of ethyl acetate at 40° C., and the ethyl acetate phase was collected.

(7) The collected ethyl acetate phase was concentrated to an extractum, and the same was dissolved by adding 3 L of deionized water to obtain an aqueous tea polyphenol solution.

(8) The aqueous tea polyphenol solution was concentrated under vacuum, with the degree of vacuum controlled above −0.080 MPa, the temperature being 52-72° C., and the aqueous product solution being concentrated to 35 Brix.

(9) The concentrated solution was dried by spray drying, and 312 g of powder product was collected.

The content of tea polyphenols was detected to 99.2% by the UV spectrophotometer common in the industry. By detection of HPLC, the content of EGC was 83.0%, and the content of EGCG+ECG of the ester catechin was 6.6%.

Embodiment 3

(1) The green tea leaves were subjected to crushing and wall-breaking treatment, and the particle size of the treated tea leaves in the range of 10-100 meshes was more than 60%.

(2) 5.0 Kg of the pretreated tea leaves were added to a dynamic extraction tank (with stirring), 4 times the volume of deionized water was added, and the pH value was adjusted to 6.0 with citric acid, with the enzymolysis performed at a rotation speed of 100 r/min and a temperature of 40° C. for 8 hours.

(3) After that, the stirring was turned off, the deionized water was added for one leaching at 80° C., and the mass ratio of tea leaves to deionized water in the extraction tank was controlled to be 1:8, with the leaching for 30 min; at the end of the first leaching, it filtered out a filtrate, and the deionized water in the same proportion was added; and the same leaching was performed for one time, it filtered after the end of leaching, and the two filtrates were combined.

(4) The collected filtrate was cooled to 40° C., further filtered by a filter with an accuracy of 200 meshes, and the filtrate was collected.

(5) The above tea water was concentrated to 1.5 Brix by a concentrating device.

(6) The above-mentioned concentrated tea water was extracted with 1.5 times the volume of ethyl acetate at an extraction temperature of 50° C. to collect an ethyl acetate phase; the ethyl acetate phase was concentrated to a solid content of 10%, and the reverse phase extraction was performed with 0.8 times the volume of deionized water (referred to as water washing), the water washing temperature being 50° C.; the water-washed phase was separated and collected, then washed with the same method for 2 times, and all the water-washed phases were collected and combined; and it was extracted by an additional 1.5 times the volume of ethyl acetate at 50° C., and the ethyl acetate phase was collected.

(7) The collected ethyl acetate phase was concentrated to an extractum, and the same was dissolved by adding 3 L of deionized water to obtain an aqueous tea polyphenol solution.

(8) The aqueous tea polyphenol solution was concentrated under vacuum, with the degree of vacuum controlled above −0.080 MPa, the temperature being 52-72° C., and the aqueous product solution being concentrated to 40 Brix.

(9) The concentrated solution was dried by spray drying, and 303 g of powder product was collected.

The content of tea polyphenols was detected to 98.3% by the UV spectrophotometer common in the industry. By detection of HPLC, the content of EGC was 80.8%, and the content of EGCG+ECG of the ester catechin was 7.5%.

In addition to the above embodiments, the present invention includes other embodiments. All technical solutions formed by equivalent transformation or equivalent replacement shall fall within the protection scope of the claims of the present invention.

The invention claimed is:

1. A preparation method of non-ester tea polyphenols rich in epigallocatechin (EGC), characterized by comprising the steps of:
    (1) pretreatment of tea leaves: using green tea leaves as raw materials, crushing and wall-breaking the tea leaves to obtain tea particles;
    (2) endogenous enzymes enzymolysis: adding the pretreated tea particles into a dynamic extraction tank, adding deionized water, and adding a food-grade acid to adjust the pH to 2.0-6.5; and under stirring conditions, performing enzymolysis on the ester tea polyphenols in the pre-treated tea particles by the hydrolytic enzymes of the tea itself;
    (3) leaching: leaching the pre-treated tea particles after polyphenols with deionized water twice, filtering after each leaching, and combining the two filtrates;
    (4) filtration: cooling the above-mentioned filtrate, filtering again, and collecting the filtrate;
    (5) concentration: concentrating the filtrate in step (4);
    (6) mobile extraction-water washing: extracting the concentrated solution in step (5) with 1-2 times volume of ethyl acetate, collecting an ethyl acetate phase, and concentrating the ethyl acetate phase to a solid content of 2-10%; then performing reverse phase extraction with 0.2-1 times volume of deionized water on the concentrated ethyl acetate phase, collecting a water-washed phase, and performing reverse phase extraction with the same method for 1-5 times, and combining the water-washed phases; and then performing extraction with 1-2 times volume of ethyl acetate for the water-washed phase, and collecting the ethyl acetate phase;
    (7) conversion and dissolving: concentrating the ethyl acetate phase finally collected in step (6) to an extractum, and then adding deionized water for dissolution to obtain a tea polyphenol aqueous solution; and (8) concentration: concentrating the aqueous tea polyphenol solution in step (7) under vacuum;

(9) drying: drying the concentrated solution in step (8) by spray drying to obtain a non-ester tea polyphenol product rich in EGC.

2. The preparation method of non-ester tea polyphenols rich in EGC according to claim 1, characterized in that 10-100 mesh screen residues of the pretreated tea particles in step (1) are not more than 40%.

3. The preparation method of non-ester tea polyphenols rich in EGC according to claim 1, characterized in that the addition amount of the deionized water in step (2) is 1-5 times the volume of the pretreated tea particles; the food-grade acid is citric acid; the stirring speed is 50-300 r/min; the enzymolysis temperature is 30-50° C.; and the enzymolysis time is 4-12 h.

4. The preparation method of non-ester tea polyphenols rich in EGC according to claim 1, characterized in that the leaching temperature in step (3) is 60-90° C., the single addition amount of deionized water is 6-10 times the mass of the pre-treated tea particles, and the single leaching time is 20-60 min.

5. The preparation method of non-ester tea polyphenols rich in EGC according to claim 1, characterized in that the cooling temperature in step (4) is 30-50° C., and the filtration accuracy is 100-300 meshes.

6. The preparation method of non-ester tea polyphenols rich in EGC according to claim 1, characterized in that the concentration in step (5) specifically comprises concentrating the filtrate from step (4) to 0.5-2.5 Brix.

7. The preparation method of non-ester tea polyphenols rich in EGC according to claim 1, characterized in that the ethyl acetate extraction temperature in step (6) is 30-60° C., and the deionized water reverse phase extraction temperature is 30-60° C.

8. The preparation method of non-ester tea polyphenols rich in EGC according to claim 1, characterized in that the concentration in step (8) specifically comprises concentrating the tea polyphenol aqueous solution in step (7) to 20-50 Brix under vacuum above −0.080 MPa at 52-72° C.

* * * * *